(12) United States Patent
Greendyk

(10) Patent No.: US 11,266,513 B2
(45) Date of Patent: Mar. 8, 2022

(54) DEVICE FOR MEASURING INTERVERTEBRAL SPACE

(71) Applicant: Stryker European Operations Limited, Carrigtwohill (IE)

(72) Inventor: Steven Greendyk, Butler, NJ (US)

(73) Assignee: Stryker European Operations Limited

( * ) Notice: Subject to any disclaimer, the term of this patent is extended or adjusted under 35 U.S.C. 154(b) by 98 days.

(21) Appl. No.: 16/702,696

(22) Filed: Dec. 4, 2019

(65) Prior Publication Data

US 2020/0197192 A1 Jun. 25, 2020

Related U.S. Application Data

(60) Provisional application No. 62/783,977, filed on Dec. 21, 2018.

(51) Int. Cl.
*A61F 2/46* (2006.01)
*A61B 17/70* (2006.01)
*A61B 17/68* (2006.01)

(52) U.S. Cl.
CPC ........ *A61F 2/4657* (2013.01); *A61B 17/7074* (2013.01); *A61F 2/4611* (2013.01); *A61B 2017/681* (2013.01); *A61F 2002/4615* (2013.01)

(58) Field of Classification Search
CPC .................. A61F 2/4611; A61F 2/4657; A61F 2002/4615; A61F 2002/4658; A61B 90/06; A61B 2090/061; A61B 2090/064
See application file for complete search history.

(56) References Cited

U.S. PATENT DOCUMENTS

| 3,667,474 | A | 6/1972 | Lapkin et al. |
| 4,038,987 | A | 8/1977 | Komiya |
| 5,113,846 | A | 5/1992 | Hiltebrandt et al. |
| 5,235,966 | A | 8/1993 | Jamner |
| 5,649,902 | A | 7/1997 | Yoon |

(Continued)

FOREIGN PATENT DOCUMENTS

| DE | 20004812 U1 | 9/2000 |
| WO | 9525485 A1 | 9/1995 |
| WO | 0141652 A1 | 6/2001 |

OTHER PUBLICATIONS

Extended European Search Report for Application No. 19216397.0 dated May 12, 2020, 3 pages.

*Primary Examiner* — Anu Ramana
(74) *Attorney, Agent, or Firm* — Lerner, David, Littenberg, Krumholz & Mentlik, LLP

(57) ABSTRACT

The present disclosure provides a device and method for measuring or distracting an intervertebral distance of an intervertebral space between a first vertebral body and a second vertebral body. The device includes a displacement unit having first and second engagement members. Displacement of the engagement members is caused by actuating an actuator on the device. In response to actuation, a force transfer carrier drives the displacement between the engagement members. The force transfer carrier is connected to the engagement members by a plurality of linkages. The distance between the engagement members is indicated by a gauge having an indicator rotatable about a pivot point. The distance between the engagement members varies in a nonlinear relationship to the movement of the force transfer carrier.

17 Claims, 8 Drawing Sheets

(56) References Cited

U.S. PATENT DOCUMENTS

| | | | |
|---|---|---|---|
| 5,656,012 A | 8/1997 | Sienkiewicz | |
| 5,713,907 A | 2/1998 | Hogendijk et al. | |
| 5,755,661 A | 5/1998 | Schwartzman | |
| 6,174,311 B1 | 1/2001 | Branch et al. | |
| 6,183,517 B1 | 2/2001 | Suddaby | |
| 6,261,296 B1 | 7/2001 | Aebi et al. | |
| 6,332,895 B1 | 12/2001 | Suddaby | |
| 6,395,031 B1 | 5/2002 | Foley et al. | |
| 6,582,451 B1 | 6/2003 | Marucci et al. | |
| 6,595,998 B2 | 7/2003 | Johnson et al. | |
| 6,676,665 B2 | 1/2004 | Foley et al. | |
| 6,840,944 B2 | 1/2005 | Suddaby | |
| 7,063,705 B2 | 6/2006 | Young et al. | |
| 7,083,650 B2 | 8/2006 | Moskowitz et al. | |
| 7,087,055 B2 | 8/2006 | Lim et al. | |
| 7,507,241 B2 | 3/2009 | Levy et al. | |
| 7,625,377 B2 | 12/2009 | Veldhuizen et al. | |
| 7,744,637 B2 | 6/2010 | Johnson et al. | |
| 7,749,273 B2 | 7/2010 | Cauthen, III et al. | |
| 7,758,644 B2 | 7/2010 | Trieu | |
| 7,828,727 B2 | 11/2010 | Bhatnagar et al. | |
| 7,901,409 B2 | 3/2011 | Canaveral et al. | |
| 8,043,295 B2 * | 10/2011 | Reed | A61B 17/025 606/90 |
| 8,252,001 B2 * | 8/2012 | Quirno | A61B 17/025 606/102 |
| 8,292,890 B2 | 10/2012 | Wu | |
| 8,328,818 B1 | 12/2012 | Seifert et al. | |
| 8,414,593 B2 * | 4/2013 | Quirno | A61F 2/4657 606/90 |
| 8,628,577 B1 | 1/2014 | Jimenez | |
| 9,393,055 B2 * | 7/2016 | Altarac | A61B 17/7062 |
| 2002/0128716 A1 | 9/2002 | Cohen et al. | |
| 2003/0171812 A1 | 9/2003 | Grunberg et al. | |
| 2003/0187453 A1 | 10/2003 | Schlapfer et al. | |
| 2003/0220650 A1 | 11/2003 | Major et al. | |
| 2004/0087994 A1 | 5/2004 | Suddaby | |
| 2004/0267279 A1 | 12/2004 | Casutt et al. | |
| 2006/0074431 A1 | 4/2006 | Sutton et al. | |
| 2006/0235423 A1 | 10/2006 | Cantu | |
| 2007/0032791 A1 | 2/2007 | Greenhalgh | |
| 2008/0183204 A1 | 7/2008 | Greenhalgh et al. | |
| 2010/0010494 A1 | 1/2010 | Quirno | |
| 2014/0107659 A1 | 4/2014 | Walters et al. | |

* cited by examiner

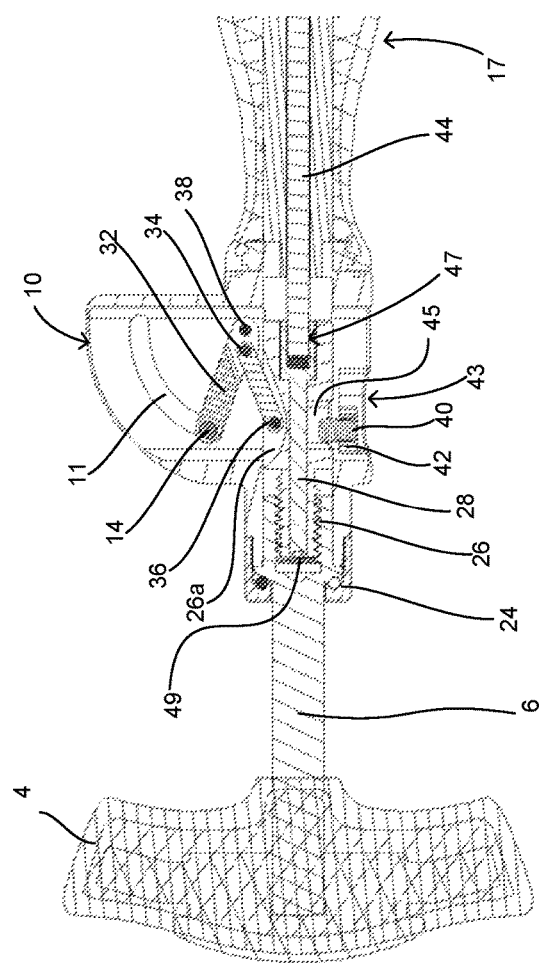
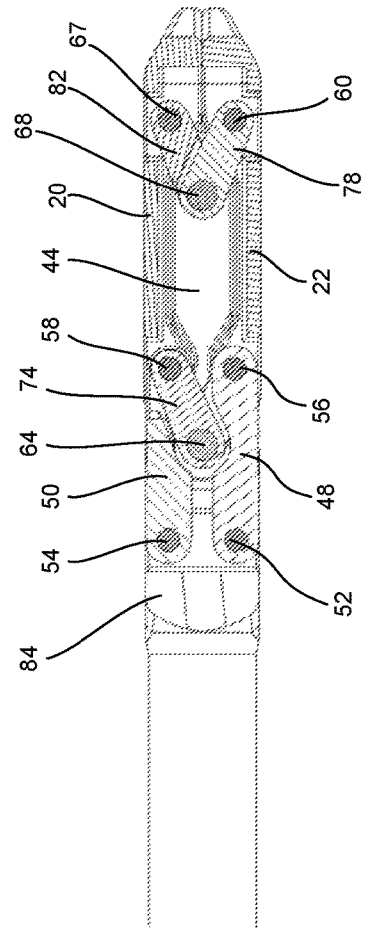
FIG. 4A
FIG. 4B

DEVICE FOR MEASURING INTERVERTEBRAL SPACE

CROSS REFERENCE TO RELATED APPLICATIONS

The present application claims the benefit of the filing date of U.S. Provisional Patent Application No. 62/783,977, filed Dec. 21, 2018, the disclosure of which is hereby incorporated herein by reference.

BACKGROUND OF THE INVENTION

The adult human spinal column is comprised of more than twenty discrete bones coupled sequentially to one another by a tri-joint complex that consists of an anterior vertebral body and the two postero-lateral facet joints, the vertebral bodies of adjacent bones being connected by spacers referred to as intervertebral discs. These more than twenty bones are anatomically categorized as being members of one of four classifications: cervical, thoracic, lumbar, or sacral.

The cervical portion of the spine, which comprises the top of the spine, up to the base of the skull, includes the first seven vertebrae. The intermediate twelve bones are the thoracic vertebrae, and connect to the lower spine comprising the five lumbar vertebrae. At the base of the spine are the sacral bones (including the coccyx). The component bones of the cervical spine are generally smaller than those of the thoracic spine, which are in turn smaller than those of the lumbar region. The sacral region connects laterally to the pelvis.

The spinal column is highly complex in that it includes these more than twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes that can result in spinal pathologies for which surgical intervention may be necessary. With respect to the failure of the intervertebral disc, and the insertion of implants and/or height restorative devices, several methods and devices have been disclosed in the prior art that achieve immobilization and/or fusion of adjacent bones by implanting artificial assemblies in or on the spinal column. The region of the back that needs to be corrected, as well as the individual variations in anatomy, determine the appropriate surgical protocol and implantation assembly.

Intervertebral implants are commonly used in spinal surgery, such as in interbody fusion procedures, in which one or more implants (e.g., a spacer or cage) are placed in the intervertebral space between two vertebrae to be fused together. Generally, the preparation of the intervertebral space for the receipt of the implants involves removing at least a portion of the damaged disc material and thereafter distracting the adjacent vertebral bones to their appropriate distance apart. Once the proper height of the intervertebral space is restored, the implant(s) can be positioned in the intervertebral space, and the implant(s) may be supplemented with bone graft material to promote fusion of the vertebrae. Such interbody fusion procedures may also be performed in conjunction with other types of fixation, such as pedicle screw fixation, to provide additional stability, particularly while the vertebrae fuse together.

Different interbody fusion procedures can be distinguished by their location along the spine (e.g., in the cervical, thoracic, or lumbar regions); by the type of implant used; and by the surgical approach to the intervertebral space, in which different surgical approaches often imply different structural characteristics of the implant or implants used. Different surgical approaches to the spine include anterior, posterior, and lateral. Examples of interbody fusion techniques performed along a posterior approach include posterior lumbar interbody fusion (PLIF) and transforaminal lumbar interbody fusion (TLIF). PLIF techniques typically include positioning two intervertebral implants into the intervertebral space along a posterior to anterior direction, with one implant being positioned towards the left side of the spine and one implant being positioned towards the right side of the spine. The implants used in such PLIF techniques typically have a straight shape, in that they extend along a central axis. TLIF techniques, by contrast, typically include positioning one intervertebral implant into the intervertebral space (often towards the anterior portion of the intervertebral space) from the posterior of the patient, but the spine is approached on one side from a more lateral position than in PLIF techniques. The implants used in such TLIF techniques are often curved, such that they have an overall kidney bean-like shape. Interbody fusion techniques performed along a lateral approach, on the other hand, often involve implants that are generally symmetric along their linear longitudinal axis (e.g., having a substantially rectangular or oval shape), but the implants are typically larger than those used in PLIF or TLIF techniques. That is, intervertebral implants used in lateral approaches often cover a substantial portion of the disc space.

It is an object of the invention to provide instrumentation and methods that enable surgeons to more accurately, easily, and/or efficiently perform a surgical procedure in an intervertebral space, including preparing the intervertebral space in connection with the implantation of one or more implants and/or determining one or more characteristics regarding the implants to be implanted. Other objects of the invention not explicitly stated will be more clearly understood in conjunction with the descriptions of the preferred embodiments disclosed hereafter.

BRIEF SUMMARY OF THE INVENTION

The present invention relates to a device and method for measuring or distracting an intervertebral distance of an intervertebral space between a first vertebral body and a second vertebral body. The measurement device has a first and second engagement member that are displaceable relative to one another within an intervertebral space by a variable distance. The first and second engagement members comprise the displacement unit of the device. When using the device, the displacement unit is positioned within an intervertebral space. The displacement of the first and second engagement members is caused by actuating an actuator on the device. Upon actuation of the actuator, a force transfer carrier moves within the device to drive the displacement of the first and second engagement members. The distance between the first and second engagement members is shown on a dial gauge. Within the dial gauge is an indicator that can rotate about a pivot point. The distance between the first and second engagement member varies in a nonlinear relationship to the movement of the force transfer carrier.

BRIEF DESCRIPTION OF THE DRAWINGS

FIG. 4A is a cross-sectional view of the proximal end of the measurement device of FIG. 1, when the paddles are at a minimum distraction height.

Figure 1:
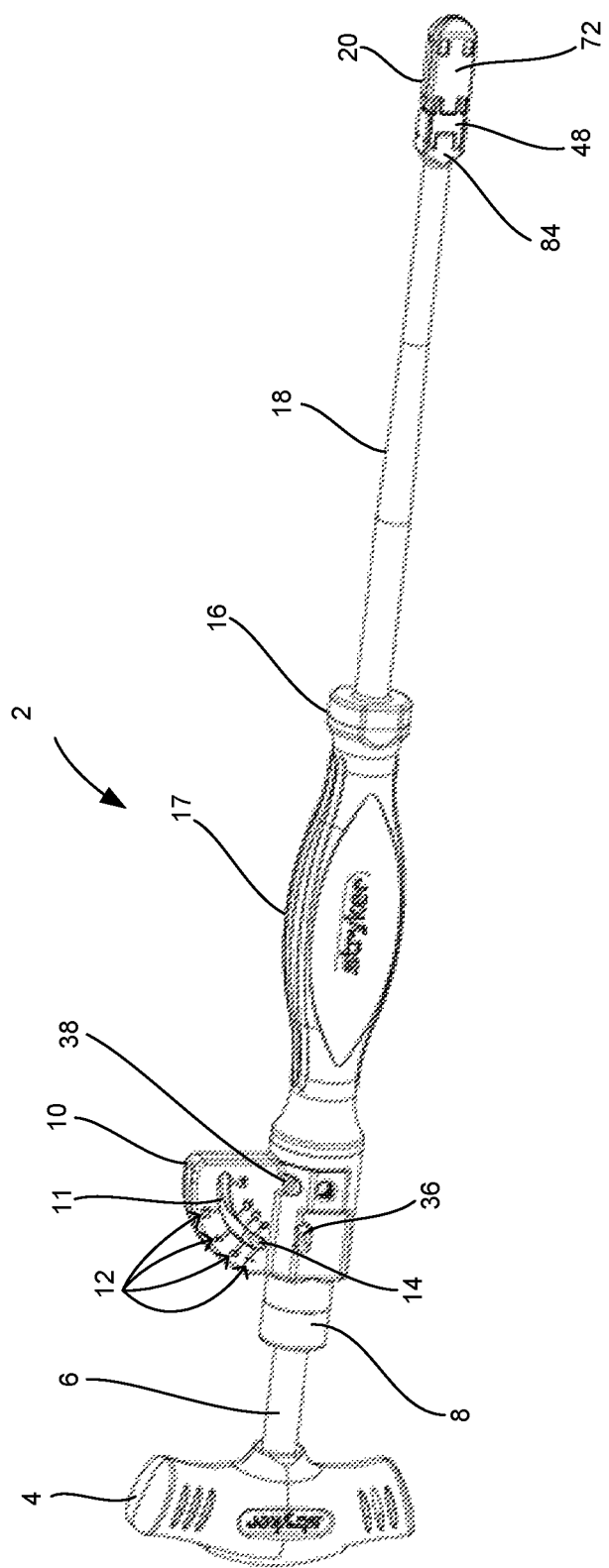
FIG. 1 is a perspective view of a measurement device in accordance with one embodiment of the present invention.

FIB. 4B is a cross-sectional view of the distal end of the measurement device of FIG. 1, when the paddles are at a minimum distraction height.

Figure 5A:
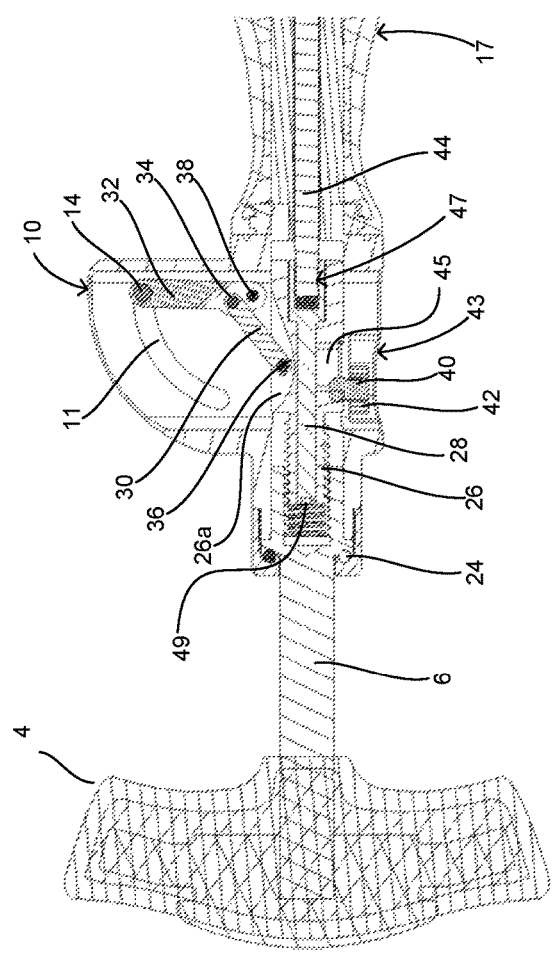

FIG. 5A is a cross-sectional view of the proximal end of the measurement device of FIG. 1, when the paddles are at a maximum distance apart.

FIB. 5B is a cross-sectional view of the distal end of the measurement device of FIG. 1, when the paddles are at a maximum distance apart.

Figure 6:
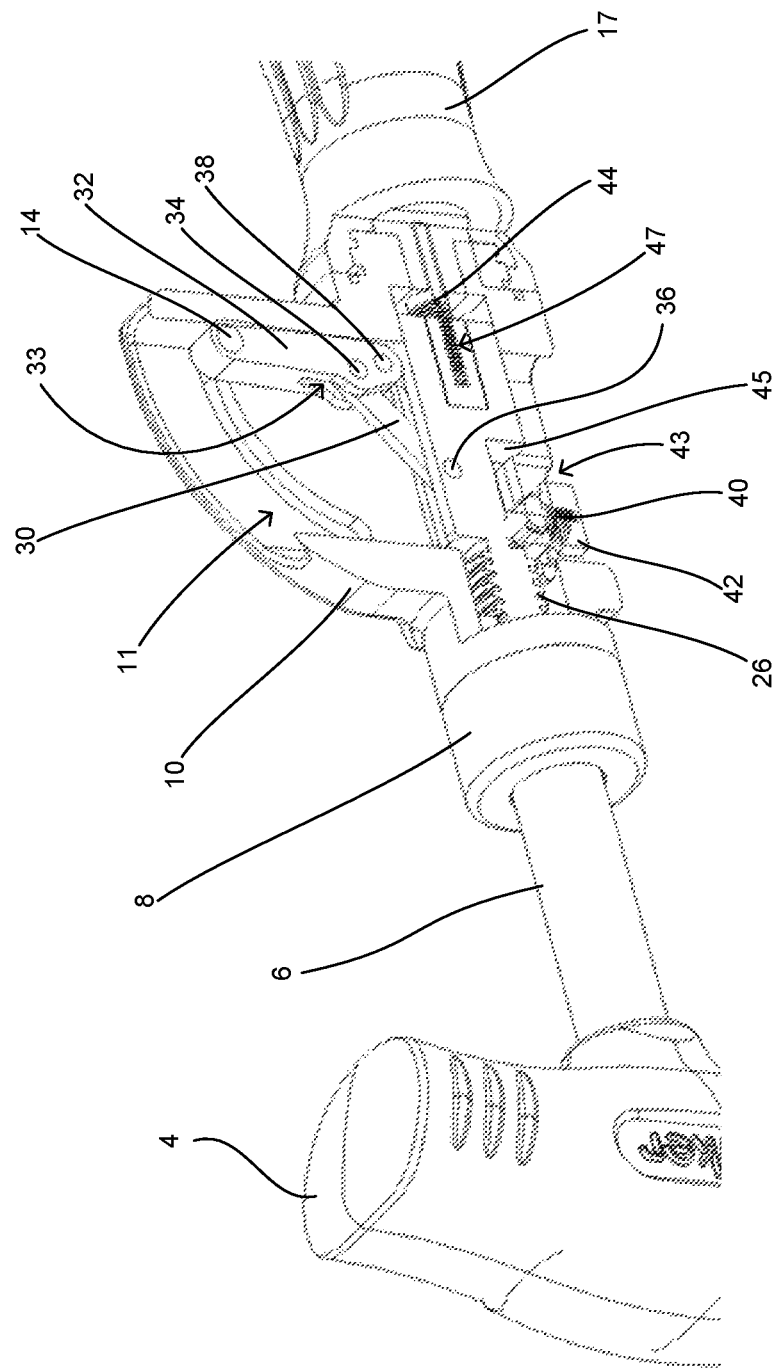

FIG. 6 is a perspective view of the proximal end of the measurement device of FIG. 1, showing a cross sectional view of a portion of the measurement display portion.

Figure 7:
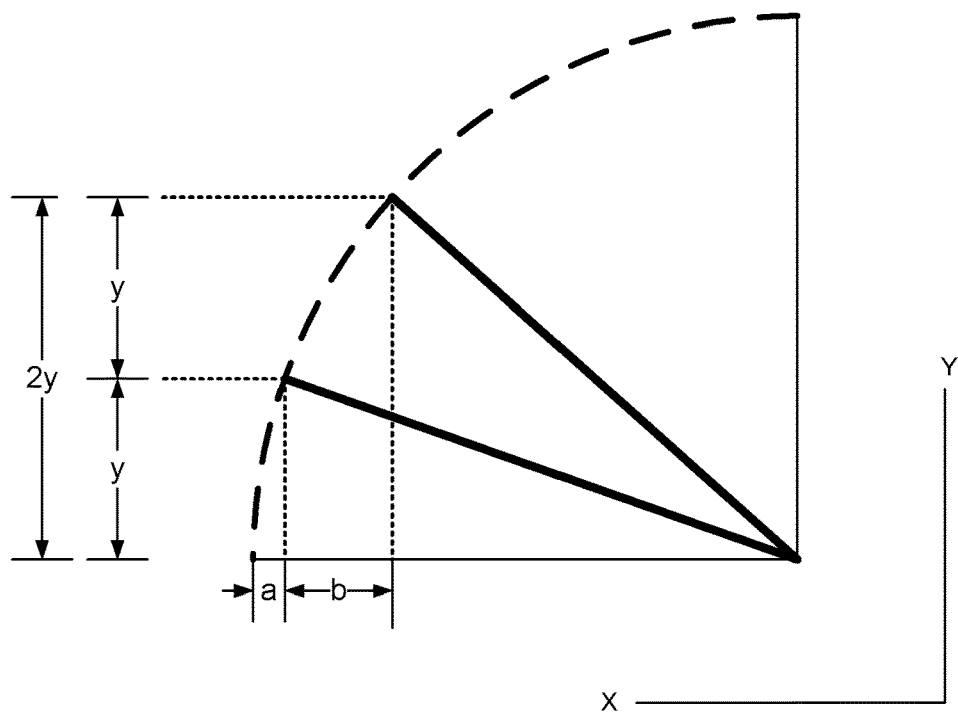

FIG. 7 is a diagram illustrating the horizontal and vertical components of movement of a rotating link.

Figure 8:
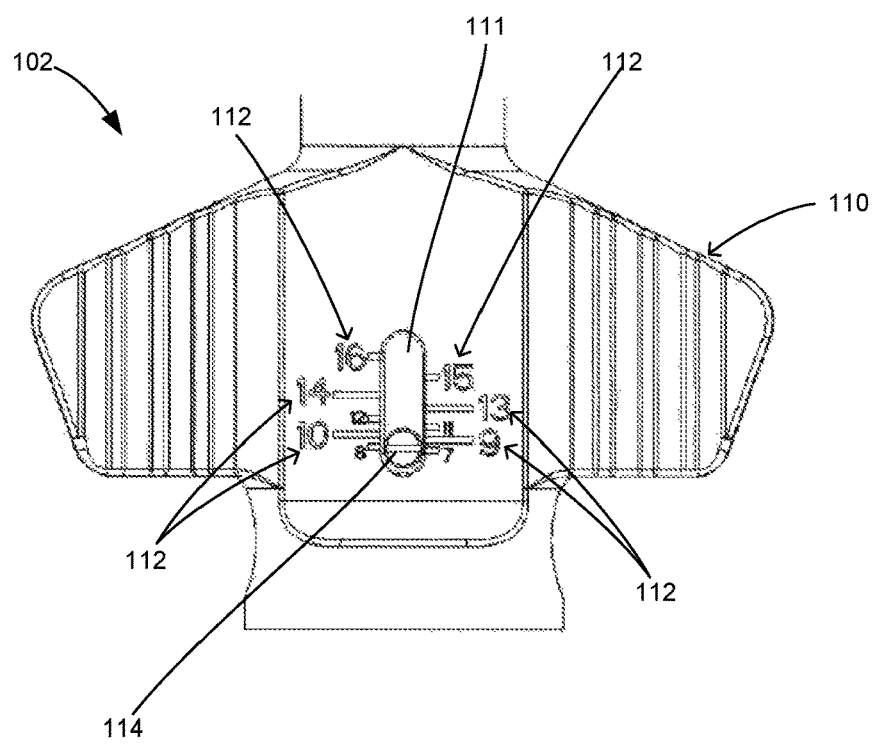

FIG. 8 is a plan view of a measurement display portion of a prior art measurement device.

DETAILED DESCRIPTION

FIG. 1 illustrates a preferred embodiment of a measurement device 2 in accordance with one embodiment of the present invention. Measurement device 2 can be used to measure an intervertebral distance between two vertebral bodies or it can be used to create additional space between two vertebral bodies by distracting them apart prior to the implantation of an interbody device. Measurement device 2 has an easy to read measurement display 10 with clearly separated graduations 12 allowing a surgeon to determine what size interbody device is needed or to be able to easily create a predetermine amount of separation between the vertebrae.

Measurement device 2 is comprised of a displacement unit (paddle assembly 19) having two engagement members (paddles 20, 22) that are displaceable relative to one another within an intervertebral space, an actuator (handle 4) to induce the displacement of the engagement members, a force transfer carrier (inner shaft 44) adapted to move within the measurement device 2 in response to the actuation of the actuator so as to drive the displacement of the engagement members, and a dial gauge or measurement display 10 having an indicator (indicator pin 14 visible via indicator slot 11).

The proximal end of the measurement device 2 has handle 4, which is a portion of the actuator, with handle shaft 6 attached to the distal end of handle 4. The distal end of handle shaft 6 extends into the body 16 of the measurement device 2 for operation of the displacement unit. Measurement display 10, which may be in the form of a dial gauge, is connected to the body 16 of the measurement device 2. The body 16 may also include a handle portion 17 and an outer shaft portion 18 that extends between the handle portion 17 and the distal end of body 16. The displacement unit is positioned at the distal end of the shaft portion 18 of the body 16. In the preferred embodiment shown, the displacement unit is paddle assembly 19. However, the displacement unit can be any embodiment that allows for distance to be created or measured.

Figure 2:
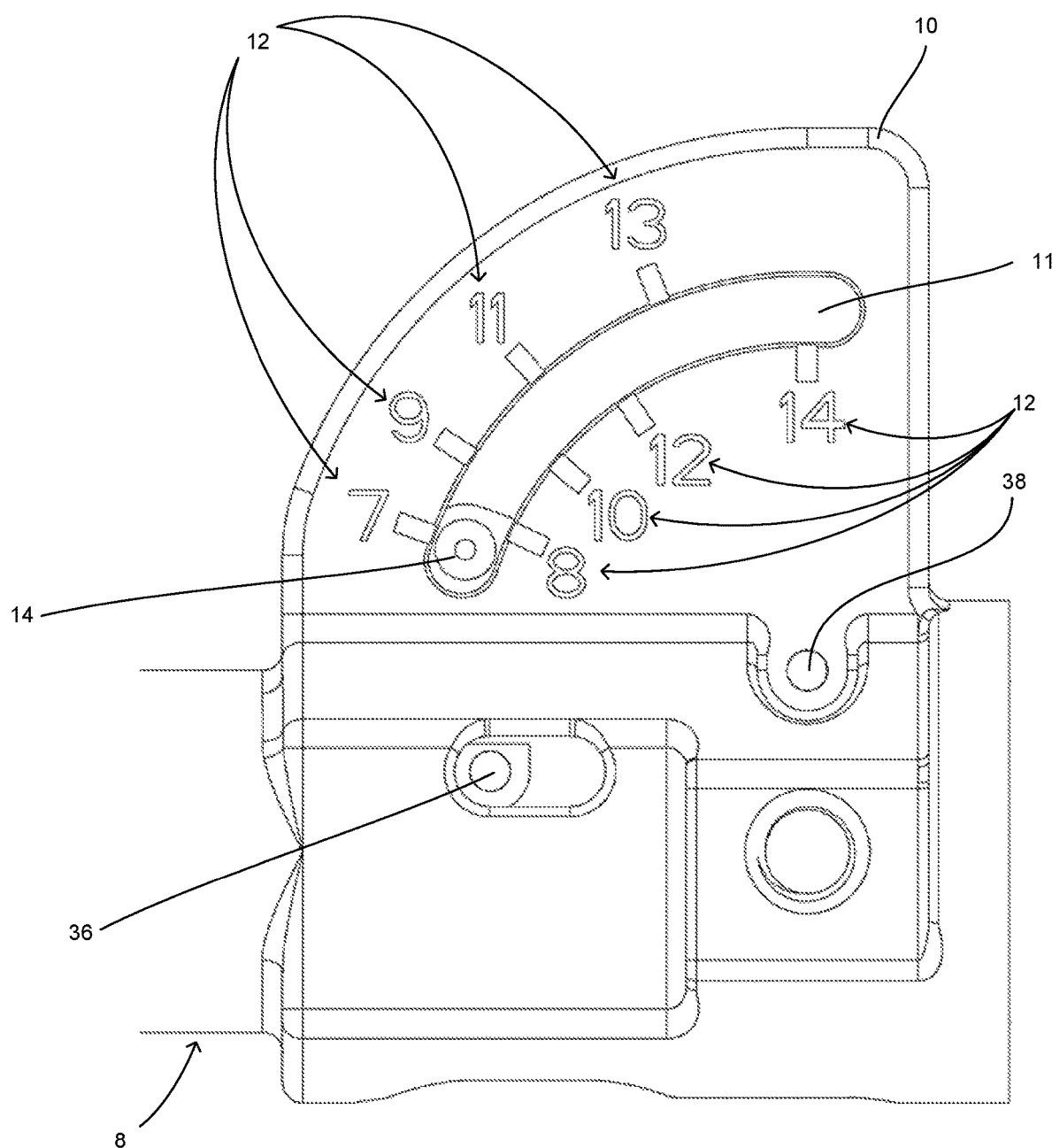
FIG. 2 is a perspective view of the measurement display portion of the measurement device of FIG. 1.

FIG. 2 illustrates a preferred embodiment of the measurement display 10 found as part of the measurement device 2. Measurement display 10 has graduations 12 which correspond to the distance between the engagement members (paddles 20, 22). The graduations 12 on measurement display 10 are along the perimeter of indicator slot 11. Within indicator slot 11 is indicator pin 14 which moves in tandem with the movement of paddles 20, 22. The indicator pin 14 will move along indicator slot 11 as the distance between paddles 20, 22 increases or decreases so that indicator pin 14 will align with the graduation 12 that corresponds to the distance between paddles 20, 22.

Figure 3A:
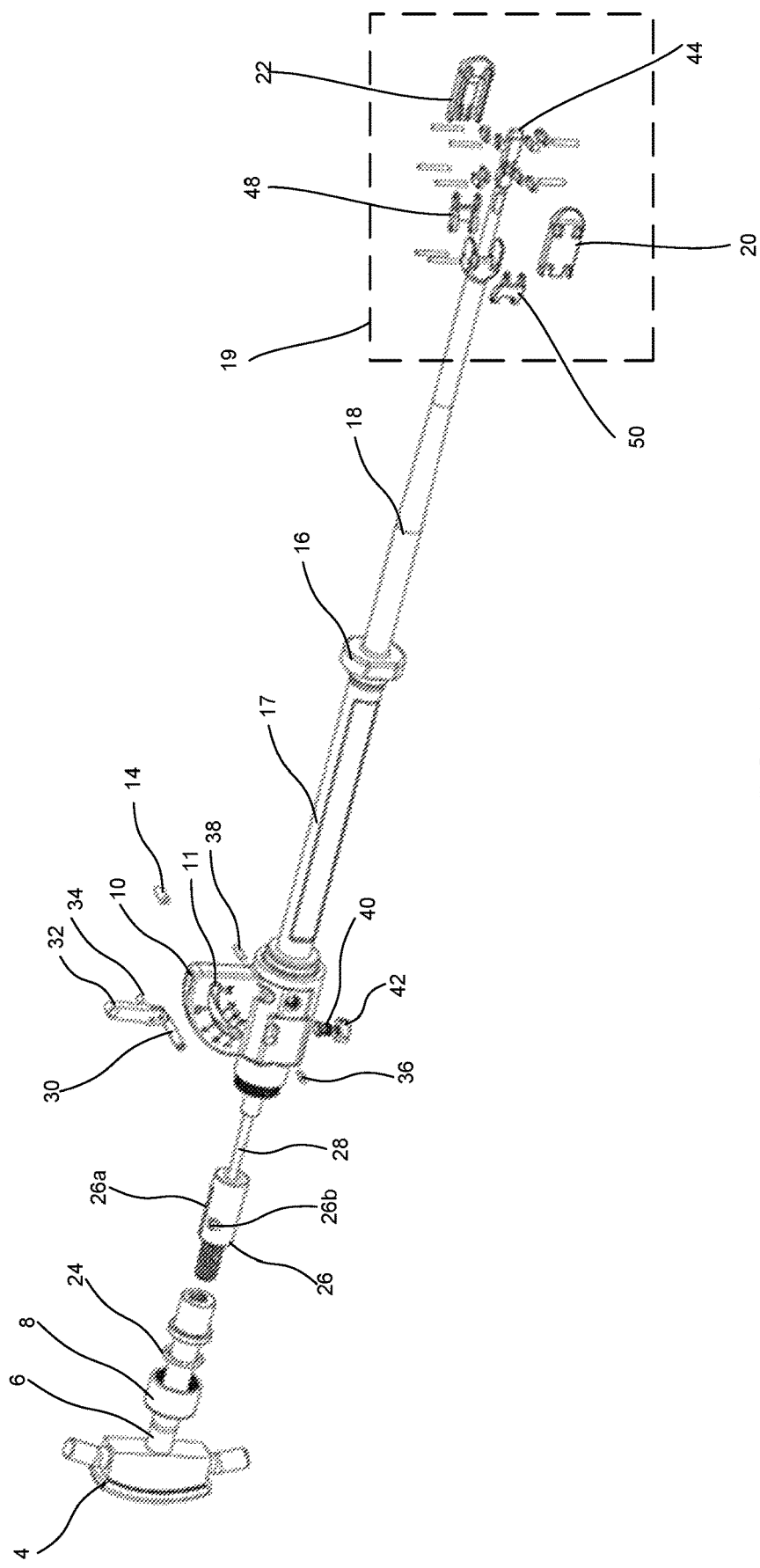
FIG. 3A is an exploded view of the measurement device of FIG. 1.
Figure 3B:
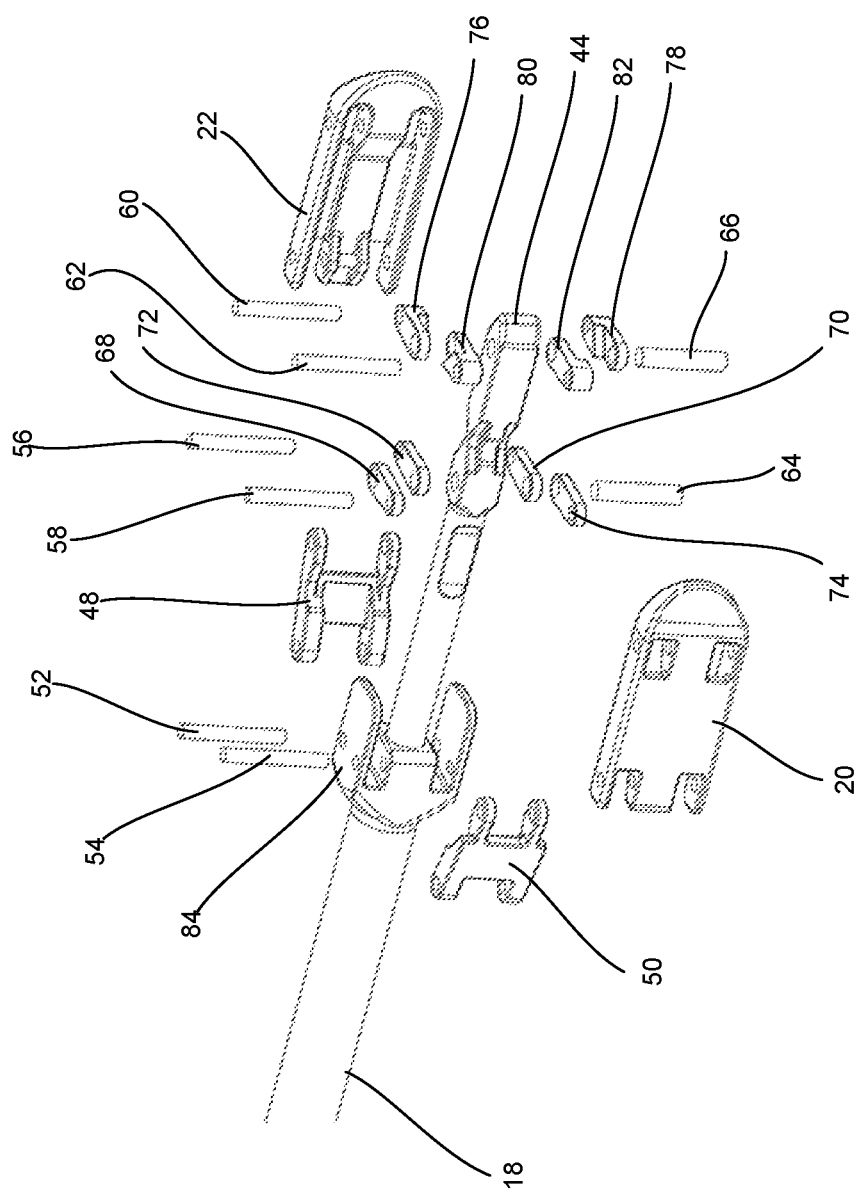
FIG. 3B is an exploded view of the paddle assembly portion of the measurement device of FIG. 3A.

FIG. 3A is an exploded view of measurement device 2. Starting at the proximal end, the measurement device 2 has a handle 4. Handle 4 acts as an actuator. In this preferred embodiment handle 4 has a "T" shape, allowing for easy gripping, but this is not meant to be limiting. The distal end of handle 4 is connected to the proximal end of handle shaft 6. The distal end of handle shaft 6 extends into the body 16 of the measurement device 2, where its longitudinal position with respect to the body 16 is restrained by end cap 8 secured to the proximal end of the body 16. The distal end of handle shaft 6 is threaded so as to be rotationally mated with the threading of slider 26. Since handle shaft 6 is rotatable with respect to the body 16 while end cap 8 remains stationary, a ball bearing 24 may be positioned between the end cap 8 and an abutting portion of the handle shaft 6 to minimize friction. Slider 26 has a slot 26a to allow for the crank-slider mechanism to operate without interference as various parts of measurement device 2 move linearly. Slider 26 also has hole 26b that allows for slider pin 36 to be inserted.

Found within slider 26 is adjustment insert 28. Adjustment insert 28 allows for measurement device 2 to be calibrated. As shown in FIGS. 4A and 5A, adjustment insert 28 has a threaded coupling 47 at its distal end that threadedly engages threads on the proximal end of the inner shaft 44, and the proximal end of the adjustment insert 28 is accessible via an opening through the proximal end of the slider 28. To calibrate the dial, the paddles 22, 20 are held in a fixed position with a known spacing between them, and the adjustment insert 28 is rotated clockwise to advance along the threads of the inner shaft 44. In order to perform that rotation of the adjustment insert 28, the adjustment insert 28 is accessed via the opening at the proximal end of slider 28 prior to the attachment of handle 4, with handle shaft 6, to the body 16 of measurement device 2. The adjustment insert 28 may be rotated by engaging a driving tool (not shown) to a driver interface 49 at the proximal end of the adjustment insert 28. This rotation advances the adjustment insert 28 distally, allowing slider 26 to advance distally, which then causes movement of the indicator pin 14, allowing the indicator pin 14 to be set to the correct graduation 12 that aligns with the known, fixed spacing of the paddles 20, 22. Once the indicator pin 14 is calibrated with respect to the spacing of the paddles 20, 22, the position of adjustment insert 28 is locked to slider 26. This may be done by welding operation, thus making them one rigid part in the final assembly. The welding operation is desirably performed prior to the attachment of handle 4, with handle shaft 6, to the body 16 of measurement device 2. The weld may be located at the proximal end surface of slider 26, where the adjustment insert 28, once inserted into the slider 26, becomes flush with the proximal end surface of the slider 26. Once the indicator pin 14 is calibrated, adjustment nut 42 is threaded onto adjustment screw 40. The adjustment screw 40 can be slid back and forth to a desired location along the slot 43, and then fixed in that location by tightening down the nut 42. The adjustment screw 40 extends into a pocket 45 on the bottom of the slider 26, and, once it is fixed, the adjustment screw 40 thus constrains the movement of the slider 26 to prevent indicator pin 14 from advancing too far on either end of the curved indicator slot 11 of the measurement display 10. That is, as shown in FIG. 4A, when the indicator pin 14 is at the lowest end of the indicator slot 11, the adjustment screw 40 abuts the distal end of the pocket 45 to prevent further movement of the slider 26 in the proximal direction. Similarly, as shown in FIG. 5A, when the indicator pin 14 is at the highest end of the indicator slot 11, the adjustment screw 40 abuts the proximal end of the pocket 45 to prevent further movement of the slider in the distal direction. The purpose of adjustment screw 40 and adjustment nut 42 is, thus, to act as a travel limiting feature to prevent damage to the slider-crank linkage within measurement display 10.

While various components of measurement display 10 are shown in FIG. 3A, the connections for the indicator are best shown in FIGS. 4A-6. Slider 26 is rigidly attached to inner shaft 44 via the adjustment insert 28. The inner shaft 44 has a proximal end beginning inside measurement display 10 and a distal end within paddle assembly 19. As the actuator is actuated, or, as shown in the preferred embodiment, as handle 4 is rotated, the threads on the distal end of handle shaft 6 threadedly advance along the threads of slider 26, causing slider 26 and inner shaft 44 to move linearly. Thus, the slider 26 and the inner shaft 44 together function as a force transfer carrier that transfers the actuation force from the handle 4 to the paddle assembly 19. The movement of slider 26 and inner shaft 44 cause the slider-crank linkage within measurement display 10 to move.

The slider-crank linkage within measurement display 10 is made up of slider pin 36, fixed pin 38, link pin 34, coupler link 30, crank link 32 and indicator pin 14. Slider pin 36 is rigidly attached to slider 26 such that coupler link 30 will rotate about slider pin 36 as slider 26 and inner shaft 44 move linearly within the body 16. The opposite end of coupler link 30 is attached to crank link 32 by way of link pin 34. Crank link 32 is rigidly fixed to measurement display 10 by way of fixed pin 38, which has a fixed position with respect to the body 16. Thus, crank link 32 will rotate about fixed pin 38 under the influence of the movement of the coupler link 30, which is in turn driven by the linear movement of the slider 26. At the end of crank link 32 opposite fixed pin 38 is indicator pin 14. Indicator pin 14 is visible within indicator slot 11 such that, as crank link 32 rotates around fixed pin 38 caused by linear movement of the slider 26 (via intermediate coupler link 30), indicator pin 14 moves within indicator slot 11 corresponding to the distraction height between paddles 20, 22. Indicator pin 14 will allow for a surgeon to be able to read the distraction height by looking at the corresponding graduations 12 on measurement display 10.

As indicator pin 14 reaches its minimum distraction height graduation 12, coupler link 30 collapses within the slot 26a of slider 26 and the notch 33 within crank link 34, as best seen in FIG. 4A. As best seen in FIG. 6, the notch 33 within crank link 34 may be a slot in the distal half of crank link 34 that is the approximately the width of coupler link 30, allowing coupler link 30 to fit within the notch 33 as crank link 32 folds on top of coupler link 30.

FIG. 4A shows the slider-crank linkage within measurement display 10 when paddles 20, 22 are closed, such that the distraction height is merely the height of paddles 20, 22 combined. Indicator pin 14 is shown at the lowest point in indicator slot 11. This is also the same indicator pin 14 position that is shown in FIG. 2. FIG. 4B shows paddle assembly 19 closed, such that paddles 20, 22 are touching.

FIG. 5A shows the slider-crank linkage within measurement display when paddles 20, 22 are at maximum separation. Indicator pin 14 is shown at the maximum point in indicator slot 11. Slider 26 can be seen as having advanced distally with respect to the body 16 (i.e., to the right in FIG. 5A) along the internal threads of the handle shaft 6. As slider 26 moves towards the distal end of measurement device 2, inner shaft 44 also moves distally as slider 26 is rigidly fixed to inner shaft 44. The linear movement of inner shaft 44 causes paddle assembly 19 to open by pushing the linkages within paddle assembly 19. In an alternative embodiment (not shown), the linkages can be mirrored such that proximal movement of the inner shaft 44 to pull the linkages within the paddle assembly 19 causes the paddle assembly 19 to open.

In the preferred embodiment, when handle 4 is rotated clockwise, paddle assembly 19 opens. In alternative embodiments, a rotation counter-clockwise can cause paddle assembly 19 to open. In other embodiments not shown, threads may not be used as part of the actuator and therefore some motion other than rotation can cause paddle assembly 19 to open.

Figure 5B:
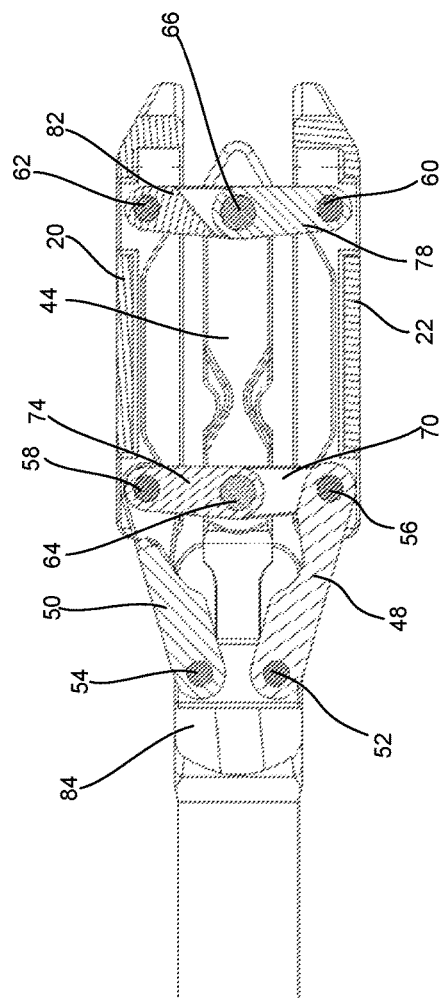

Turning to the operation of the displacement unit, the paddle assembly 19 is structured such that distal advancement of the inner shaft 44 pushes paddle links 68, 70, 72, 74, 76, 78, 80, 82 towards their extended configuration shown in FIG. 5B. Paddle links 70, 72, 76, 78 connect paddle 22 to inner shaft 44. A paddle support link 48 is attached, at its proximal end, to paddle base 84 via paddle support pin 52, and the distal end of paddle support link 48 is attached to paddle 22 via paddle pin 56. Paddle base 84 is attached to handle assembly 18. Paddle support link 48 can rotate around paddle support pin 52. The paddle pin 56 that attaches the distal end of paddle support link 48 to the paddle 22 can also attach the paddle links 70, 72 to the proximal end of paddle 22. Paddle support link 48 and paddle links 70, 72 can rotate around paddle pin 56. The ends of paddle links 70, 72 opposite paddle pin 56 are connected to inner shaft 44 via inner shaft pin 64. Paddle links 68, 74 are also connected to inner shaft 44 via inner shaft pin 64. Paddle links 68, 70, 72, 74 can rotate around inner shaft pin 64. The end of paddle links 68, 74 opposite inner shaft pin 64 are connected to the proximal end of paddle 20 via paddle pin 58. The distal end of paddle support link 50 can also be connected to the proximal end of the paddle 20 via paddle pin 58. Paddle links 68, 74 and paddle support link 50 can rotate around paddle pin 58. The proximal end of paddle support link 50 is connected to paddle base 84 via paddle support link pin 54. Paddle support link 50 can rotate around paddle support link pin 54.

Paddle links 76, 78, 80, 82 work in unison with paddle links 68, 70, 72, 74 to ensure that paddles 20, 22 remain parallel to one another. Thus, when paddle links 68, 70, 72, 74 extend, paddles links 76, 78, 80, 82 also extend. The same holds true when the paddles links 68, 70, 72, 74 begin to collapse in on each other as inner shaft 44 moves from the distal end of dynamic device 2 towards the proximal end.

Paddle links 76, 78 are connected to paddle 22 via paddle pin 60. This connection is located towards the distal end of paddle 22. The location of the connection shown in FIGS. 4B and 5B is merely one option and is not meant to be limiting. Paddle links 76, 78 can rotate around paddle pin 60, allowing paddle links 76, 78 to fold and unfold as inner shaft 44 is moved. Paddle links 76, 78 as well as paddle links 80, 82 are connected to inner shaft via inner shaft pin 66. Paddle links 76, 78, 80, 82 can rotate around inner shaft pin 66. Paddle links 80, 82 are connected to paddle 20 via paddle pin 62. This connection is located towards the distal end of paddle 22. The location of the connection shown in FIGS. 4B and 5B is merely one option and is not meant to be limiting. Paddles links 80, 82 can rotate around paddle pin 62.

In the preferred embodiment, the plurality of paddle links are configured to be able to collapse, or lay flat, on top of one another. As seen in FIG. 5B, a plurality of the paddle links are have cut outs to allow for the corresponding paddle links to collapse on top of one another when the links rotate to the collapsed position shown in FIG. 4B. This allows for the paddle assembly to have a smaller profile and it also reduces the transmission of torque through the pins. It can be seen, for example, that paddle link 82 is notched to allow for paddle link 78 to collapse on top of paddle link 82 when paddle links 68, 70, 72, 74, 76, 78, 80, 82 are in their minimum distraction position. In other embodiments, not shown, the plurality of paddle links do not require any or all links to have cut outs in them.

As inner shaft 44 advances linearly, inner shaft 44 uses a pushing motion to push open paddle assembly 19. Paddle assembly 19 uses a series of links and pins to cause displacement between paddles 20, 22. In a preferred embodiment, the movement of the inner shaft 44 causes paddle links 68, 70, 72, 74 to rotate around inner shaft pin 64 while paddle links 76, 78, 80, 82 rotate around inner shaft pin 66, which causes the rotating paddle links to push the paddles 20, 22 apart so as to increase the distance between the paddles. That displacement of the paddles 20, 22 also causes the paddle support links 48, 50 to rotate away from one another about paddle base 84, as shown in FIG. 5B.

As handle 4 is rotated and slider 26 and inner shaft 44 move linearly, paddles 20, 22 increase their distance apart in a nonlinear relationship to the linear movement of those previously-mentioned parts. This nonlinear relationship is exemplified by varied spacing between the graduations 12 on measurement display 10, and it will now be explained with reference to FIG. 7.

FIG. 8, which includes an arc A having a radius R, illustrates the non-linear relationship between the linear distance traveled by slider 26 and the vertical displacement of the paddles 20, 22. Radius R can be taken to represent the fixed length of any one of the rotating paddle links in paddle assembly 19 or the fixed length of the crank link 32 of the measurement display 10. Arc A thus represents the arc swept out by the rotating paddle links or the rotating crank link 32 as the paddles 20, 22 are displaced. Distances "a," "b," and any subsequent distances along the x-axis represent the linear movement of slider 26. Distances along the y-axis represent the vertical displacement of paddles 20, 22. Increments "y" also correspond to the height increments (graduations 12) along indicator slot 11. For each height increment "y" along indicator slot 11, the associated linear movement, "a" and "b," of slider 26 changes by a different amount. That is, the initial height increments will initially be located close together along the x-axis. However, as slider 26 continues to move along the x-axis, each subsequent height increment will continue to be more and more spread out as the links in paddle assembly 19 rotate towards a vertical orientation.

The rotational arrangement of the slider-crank linkage allows for graduations 12 to be spaced apart to allow for easier reading by the surgeon. In contrast, FIG. 8 shows the measurement display of a prior art measurement device, where the graduations 112 are defined along a linear slot that extends along the longitudinal axis of the body of the device. The indicator pin 114 could be coupled to the force transfer carrier such that both components move together linearly along the device body. Thus, due to the principles explained above in connection with FIG. 7, the initial graduations 112 representing vertical height units are spaced much more closely together than later graduations 112. In contrast, by converting the linear motion of the force transfer carrier to rotary motion of the indicator pin 14, as provided by the present invention, those initial graduations 12 can be spaced further apart than in the prior art device of FIG. 8, thus resulting in a measurement display that is easier to read than that of FIG. 8. One reason for that is that, due to the arcuate shape of the indicator slot 10, those initially small distances in the horizontal direction are associated with relatively large distances in the vertical direction, thus causing the graduations 12 to have relatively large spacing along the circumferential direction of the indicator slot 11.

The surgeon can thus use measurement device 2 to determine an intervertebral distance, so as to be able to select the most appropriate size of an interbody device to be implanted. In particular, the paddle assembly 19 of the measurement device 2 can be inserted into an intervertebral space between two vertebrae of a patient's spine (e.g., after at least a portion of the damaged disc material has been removed from the intervertebral space). Then, the actuator can be actuated (e.g., the handle 4 rotated) to drive the separation of the paddles 20, 22 until they engage the opposing vertebrae. At that point, the distance displayed on the measurement display 10 will indicate the height of the intervertebral space from one vertebral body to the other. In an alternative (or additional) method, the surgeon can use measurement device 2 to increase the intervertebral distance. Specifically, by further actuating the actuator, the paddles 20, 22 may apply a force to the vertebrae to distract them apart, so as to further increase the height of the intervertebral space. The measurement display 10 will thus indicate that distracted height produced by the expansion of the paddle assembly 19. Other uses of measurement device 2 exist, even if not described herein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A measurement device for measuring an intervertebral distance of an intervertebral space between a first vertebral body and a second vertebral body, comprising:
a displacement unit having a first engagement member and a second engagement member, the first and second engagement members being displaceable relative to one another within the intervertebral space by a variable distance until the first engagement member engages the first vertebral body and the second engagement member engages the second vertebral body;
an actuator adapted to be actuated by a user to induce the displacement of the first and second engagement members relative to one another;
a force transfer carrier adapted to move within the measurement device in response to actuation of the actuator so as to drive the displacement of the first and second engagement members; and a dial gauge having an indicator for indicating the distance between the first engagement member and the second engagement member, wherein the indicator is rotatable about a pivot point;

wherein the measurement device is configured such that the distance between the first engagement member and the second engagement member varies in a nonlinear relationship to the movement of the force transfer carrier, and wherein the indicator moves by way of a slider-crank linkage within the dial gauge, the slider-crank linkage being connected to the force transfer carrier.

2. The measurement device of claim 1, wherein the actuator is a rotatable handle.

3. The measurement device of claim 2, wherein the rotatable handle has threads that engage with the force transfer carrier such that the rotation of the handle will result in a linear displacement of the force transfer carrier.

4. The measurement device of claim 1, wherein the indicator is visible via a slot in the dial gauge.

5. The measurement device of claim 1, wherein a linear displacement of the force transfer carrier is translated into a rotational displacement of the indicator.

6. The measurement device of claim 1, wherein the first and second engagement members are connected to the force transfer carrier by a plurality of pivotable linkages, such that when the force transfer carrier moves linearly the plurality of pivotable linkages pivot to cause the first and second engagement members to be displaced relative to one another.

7. The measurement device of claim 1, further comprising an adjustment device for calibrating the indicator with respect to the distance between the first engagement member and the second engagement member.

8. The measurement device of claim 1, wherein the displacement unit is configured to apply force to the first and second vertebral bodies via the first and second engagement members such as to separate them further from each other.

9. A method of using a measurement device for measuring an intervertebral distance of an intervertebral space between a first vertebral body and a second vertebral body, the method comprising:

positioning a displacement unit of a measurement device into the intervertebral space, the displacement unit having a first engagement member and a second engagement member;

moving a force transfer carrier within the measurement device to drive displacement of the first and second engagements members relative to one another; and displaying a measurement via an indicator on a dial gauge, the indicator indicating the distance between the first engagement member and the second engagement member, wherein the indicator is rotatable about a pivot point, and wherein the indicator moves by way of a slider-crank linkage within the dial gauge, the slider-crank linkage being connected to the force transfer carrier;

wherein the distance between the first engagement member and the second engagement member driven by the movement of the force transfer carrier varies in a nonlinear relationship to the movement of the force transfer carrier.

10. The method of claim 9, wherein actuating an actuator causes the force transfer carrier to move.

11. The method of claim 10, wherein rotating a handle actuates the actuator.

12. The method of claim 9, further comprising driving the displacement of the first and second engagement members until the first engagement member contacts the first vertebral body and the second engagement member contacts the second vertebral body.

13. The method of claim 12, further comprising distracting the first and second vertebral bodies by driving further displacement of the first and second engagement members.

14. The method of claim 9, further comprising reversing the movement of the force transfer carrier, such that the first and second engagement members are no longer displaced relative to one another.

15. The method of claim 14, further comprising removing the measurement device after measuring the intervertebral distance or distracting an intervertebral distance.

16. The method of claim 15, further comprising inserting an implant, wherein the size of the implant corresponds to the measurement displayed on the dial gauge.

17. A measurement device for measuring an intervertebral distance of an intervertebral space between a first vertebral body and a second vertebral body, comprising:

a displacement unit having a first engagement member and a second engagement member, the first and second engagement members being displaceable relative to one another within the intervertebral space by a variable distance until the first engagement member engages the first vertebral body and the second engagement member engages the second vertebral body;

an actuator adapted to be actuated by a user to induce the displacement of the first and second engagement members relative to one another;

a force transfer carrier adapted to move within the measurement device in response to actuation of the actuator so as to drive the displacement of the first and second engagement members; and a dial gauge having an indicator for indicating the distance between the first engagement member and the second engagement member, wherein the indicator is rotatable about a pivot point;

wherein the measurement device is configured such that the distance between the first engagement member and the second engagement member varies in a nonlinear relationship to the movement of the force transfer carrier, and wherein the indicator is visible via a slot in the dial gauge.

* * * * *